US008771645B2

(12) United States Patent
Cordeiro et al.

(10) Patent No.: US 8,771,645 B2
(45) Date of Patent: Jul. 8, 2014

(54) COMPOSITION COMPRISING A CELL DEATH MARKER AND A WAVELENGTH-OPTIMIZED LABEL

(75) Inventors: Francesca Cordeiro, London (GB); Stephen Moss, London (GB); Frederick Fitzke, London (GB)

(73) Assignee: UCL Business PLLC, London (GB)

( * ) Notice: Subject to any disclaimer, the term of this patent is extended or adjusted under 35 U.S.C. 154(b) by 367 days.

(21) Appl. No.: 12/808,012

(22) PCT Filed: Dec. 15, 2008

(86) PCT No.: PCT/GB2008/004156
§ 371 (c)(1),
(2), (4) Date: Jul. 21, 2010

(87) PCT Pub. No.: WO2009/077750
PCT Pub. Date: Jun. 25, 2009

(65) Prior Publication Data
US 2010/0284922 A1     Nov. 11, 2010

(30) Foreign Application Priority Data

Dec. 14, 2007 (GB) .................................. 0724412.2

(51) Int. Cl.
*A61B 10/00* (2006.01)
*A61B 5/00* (2006.01)
*A61B 8/00* (2006.01)
*A61K 51/08* (2006.01)
*A61K 49/00* (2006.01)

(52) U.S. Cl.
CPC ............... *A61K 51/087* (2013.01); *A61K 51/08* (2013.01); *A61K 49/0004* (2013.01); *A61K 49/0056* (2013.01)
USPC ......... 424/9.6; 424/1.11; 424/1.65; 424/1.69; 424/9.1; 424/9.2

(58) Field of Classification Search
CPC ........... A61K 2123/00; A61K 2121/00; A61K 51/0478; A61K 51/088; A61K 51/0497; A61K 51/00; A61K 51/02; A61K 51/04; A61K 51/06; A61K 51/08; A61K 51/087; A61K 38/00; A61K 49/004; A61K 49/0032; A61K 49/0054; A61K 49/0056; A61K 49/0021; A61K 49/00; A61K 49/001; A61K 49/0017; A61K 49/0019; A61K 49/0023; A61K 49/005; A61K 49/0052
USPC ........... 424/1.11, 1.49, 1.65, 1.69, 1.73, 1.81, 424/1.85, 9.1, 9.6, 9.2; 530/350, 300; 514/1, 1.1, 21.2, 21.3
See application file for complete search history.

(56) References Cited

U.S. PATENT DOCUMENTS

| 2004/0022731 | A1* | 2/2004 | Bogdanov et al. ............. 424/9.6 |
| 2004/0162423 | A1  | 8/2004 | Czerney et al. |
| 2006/0134001 | A1* | 6/2006 | Frangioni ..................... 424/9.6 |

FOREIGN PATENT DOCUMENTS

| EP | 1425858 A | 6/2004 |
| WO | 03105814 A | 12/2003 |
| WO | 2004006963 A | 1/2004 |
| WO | WO2004/006963 | * 1/2004 |

OTHER PUBLICATIONS

Li-Cor Biosciences, 2011, Structure of IRDye 800CW.*
Li-Cor Biosciences, Dec. 19, 2006, 'New Infrared Fluorescent Reagent Product', press release document (1 page).*
Li-Cor Biosciences, Sep. 10, 2007, 'Li-Cor Infrared Dye Successfully Completes Toxicity Studies', press release document (1 page).*
Li-Cor Biosciences, Feb. 7, 2006, 'LiCor Biosciences Introductes New Line of IR-Labeled Secondary Antibodies', press release document (1 page).*
Li-Cor Biosciences, 2013, Press Release Document Summary (3 pages).*
Li-Cor Biosciences, 2010, IRDye Infrared Dyes Brochure (20 pages).*
Mass et al., "Assessment of rat and mouse RGC apoptosis imaging in vivo with different scanning laser ophthalmoscopes," Current Eye Research, vol. 32, No. 10, Oct. 2007, pp. 851-861.
Coreiro et al., "Real-time imaging of single nerve cell apoptosis in retinal neurodegeneration," Proceedings of the National Academy of Sciences of the United States of America, vol. 101, No. 36, Sep. 7, 2004, pp. 13352-13356.
Coreiro et al., "In sickness and in health: Real-Time assessment of healthy and diseased retinal ganglion cells (RGCs) in vivo," IOVS, vol. 46, no. Suppl. S, 2005, p. 4822.
Chen et al., "Nanoceria Particles Confer Neuroprotection in Retinal Cells in vitro," Invest Ophthalmol Vis Sci, vol. 46, no. Suppl.S, Jan. 1, 2005, p. 186.
Schmitz-Valckenberg et al., "Real-time in vivo imaging of retinal cell apoptosis after laser exposure," Investigative Ophthalmology * Visual Science, vol. 49, No. 6, Jun. 2008, pp. 2773-2780.
ISA/EPO, International Search Report and Written Opinion for International Application No. PCT/GB2008/004156, completed Mar. 24, 2009.

* cited by examiner

*Primary Examiner* — D L Jones
(74) *Attorney, Agent, or Firm* — Stites & Harbison PLLC; Mandy Wilson Decker

(57) ABSTRACT

The invention relates to the use of a cell death marker labelled with a wavelength-optimised label for identifying cell death in the eye. Suitable cell death markers are the Annexins and fragments and derivatives thereof. The invention also relates to a pharmaceutical composition comprising a cell death marker labelled with a wavelength-optimised label and a method for monitoring cell death in the eye using a cell death marker labelled with a wavelength-optimised label.

24 Claims, 14 Drawing Sheets

Histology image    Intravitreal Annexin 488    In vivo image

Histology image     IV Annexin 488     In vivo image

Baseline in vivo image   Annexin Alexa Fluor 555   In vivo image 2hrs after SSP

Histology image     Annexin 5 DY776     In vivo image

Histology image     Annexin 5 IRDye 800     In vivo image

Annexin 5 IRDye 800     Annexin 5 Dy-781     Annexin 5 Dy-776

Baseline in vivo image    Annexin 11 Dy776    In vivo image 2hrs after SSP

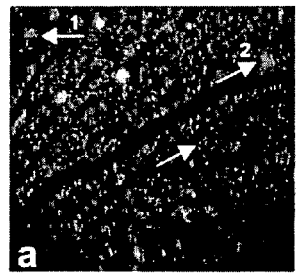 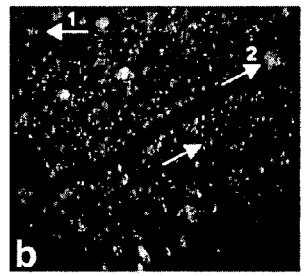 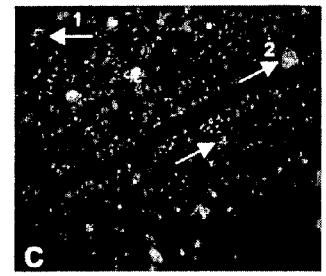
FIG. 19A      FIG. 19B      FIG. 19C
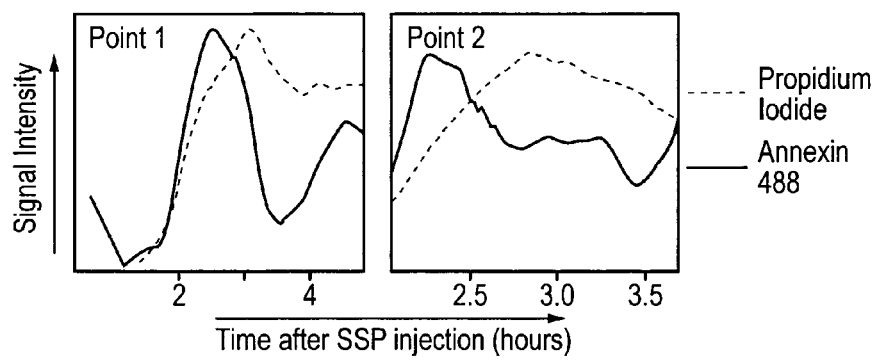
FIG. 19D
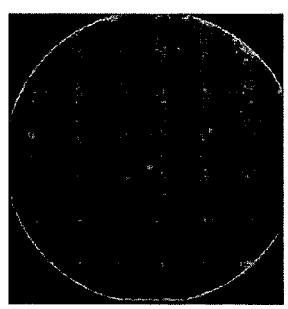 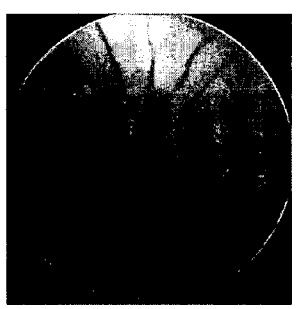 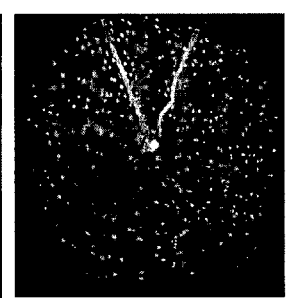
Baseline      MC540 after Saline      Annexin 776 after Saline
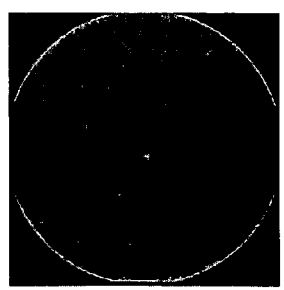 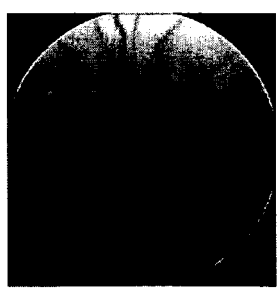 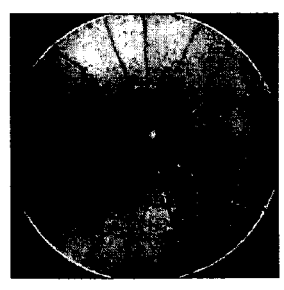
Baseline      MC540 after SSP      Annexin 776 after SSP
FIG. 20

COMPOSITION COMPRISING A CELL DEATH MARKER AND A WAVELENGTH-OPTIMIZED LABEL

The invention relates to the marker for use in the direct visualisation of cell death, particularly apoptosis in the eye, especially single cell death of retinal nerve cells.

Live cell imaging to detect cellular processes is used in in vitro assays of cultured cells. However, this has not previously been applied at the cellular level in vivo in the eye. Nerve cell loss is a process that occurs in the earliest stages of certain neurodegenerative disorders such as glaucoma, diabetic retinopathy and Alzheimer's. Glaucoma is the major cause of irreversible blindness throughout the world, affecting 2% of people over 40. The condition has a significant morbidity due to its silent and progressive nature, often resulting in a delay in diagnosis and treatment. Alzheimer's Disease is the commonest single form of dementia predicted to increase from affecting 4 to 12 million Americans over the next 20 years. It would be useful to be able to assess retinal nerve cell apoptosis in order to evaluate the progression of diseases such as glaucoma, as well as degenerative brain diseases.

By optimisation of a marker to detect cell death, administration of the marker and the imaging machine, which has lead to the development of the technology, the inventors have been able to demonstrate that single cell visualisation of apoptosis in the eye is possible. The inventors have overcome significant drawbacks including intrinsic retinal autofluorescence and negative effects such as inflammatory responses to the marker.

According to the invention there is provided the use of a cell death marker conjugated to a wavelength-optimised label for identifying cell death in the eye. The wavelength-optimised label developed provides improved image quality by improving the signal-to-noise ratio and at the same time reduces the toxic effect associated with other labels.

Also provided is a method of identifying or monitoring cell death in the eye comprising administering a cell death marker labelled with or conjugated to a wavelength-optimised label to a subject and generating an image of emission wavelength from the subject's eye using an optimised imaging device. This enables the quantification of cell death at the level of individual cells in the eye in real time.

The term 'cell death' refers to any process including, for example, death of a cell by apoptosis and necrosis, during which there is loss of plasma membrane integrity. The invention allows cells that are dying, for example undergoing apoptosis, to be identified.

The term 'cell death marker' refers to a marker that allows live cells to be distinguished from cells that are dying or have died. For example it may be a compound or molecule that specifically binds to live cells but not to dead or dying cells, or that specifically binds to dead or dying cells but not to live cells. Cell death markers include, for example the annexin family of proteins. Annexins are proteins that bind reversibly to cellular membranes in the presence of cations. Annexins useful in the invention may be natural or may be recombinant. The protein may be whole or maybe a functional fragment, that is to say a fragment or portion of an annexin that binds specifically to the same molecules as the whole protein. Also, functional derivatives of such proteins may be used. A variety of annexins are available, such as those described in US Patent Application Publication No. 2006/0134001A. A preferred annexin is Annexin 5, which is well known in the art. Other annexins that may be used as cell death markers include Annexins 11, 2 and 6. Other markers of cell death especially apoptosis, are known in the art including for example propidium iodide and the C2A domain of synaptotagmin [Jung et al., Bioconjing Chem. 2004 September-October; 15(5): 983-7].

The term 'wavelength-optimised label' refers to a fluorescent substance, that is a substance that emits light in response to excitation, and which has been selected for use due to increased signal-to-noise ratio and thereby improved image resolution and sensitivity while adhering to light exposure safety standard to avoid phototoxic effects. Optimised wavelengths include infrared and near-infrared wavelengths. Such labels are well known in the art and include dyes such as IRDye700, IRDye800, Dy-776 and Dy-781. Also included are fluorescent substances formed by conjugating such dyes to other molecules such as proteins and nucleic acids. It is preferred that optimised wavelengths cause little or no inflammation on administration. A preferred wavelength-optimised label is Dy-776, as this has been found to cause little or no inflammation in the eye, whereas other dyes can cause inflammation. Optimised dyes also preferably demonstrate a close correlation between the level of fluorescence that may be detected histologically and that which may be detected in vivo. It is particularly preferred that there is a substantial correlation, especially a 1:1 correlation between the histological and in vivo fluorescence.

The labelled cell death marker may be prepared using standard techniques for conjugating a wavelength-optimised label to a marker compound. Such labels may be obtained from well known sources such as Dyomics. Appropriate techniques for conjugating the label to the marker are known in the art and may be provided by the manufacturer of the label.

In order to generate an image of cell death, the labelled marker is administered to the subject, by, for example, intravenous injection. The area of the subject to be imaged, the eye, is placed within the detection field of a medical imaging device. Emission wavelengths from the labelled marker are then imaged and an image constructed so that a map of areas of cell death is provided. Generation of the image may be repeated to allow cell death to be monitored over a period of time. It may be monitored in real time. It is particularly preferred to monitor cell death of retinal cells, especially retinal nerve cells. Retinal nerve cells include retinal ganglion cells, bipolar, amacrine, horizontal and photoreceptor cells.

The labelled cell death marker may be administered locally or systemically. Methods for administering the marker are well known in the art and include, for example, intravenous injection. Although labelled cell death markers have been administered intravenously, the inventors have discovered surprisingly that they do cross the blood retinal barrier enabling visualisation in the eye. Previous work showed that Alexa Fluor 488 nm dye could not be seen in vivo following intravenous administration, even though its ability to cross the blood retinal barrier was demonstrated histologically. Alternatively, although less preferred, the labelled cell death marker may be administered topically or ocularly.

Also provided is a pharmaceutical composition, especially a diagnostic composition, comprising a cell death marker labelled with a wavelength-optimised marker, the composition being arranged so as to be suitable for intravenous delivery. Alternatively, although less preferred, the composition can be suitable for ocular or topical administration.

The invention will now be described in detail, by way of example only, with reference to figures, in which:

BRIEF DESCRIPTION OF THE DRAWINGS

FIG. 1 shows the correlation between in vivo imaging and histological retinal ganglion cell apoptosis when using fluorophores that are not affected by retinal autofluorescence, enabling for example, the performance of single cell apoptosis counts in vivo that correspond exactly to that seen in the gold standard of histology.

FIG. 19 contains images of a rat eye treated with staurosporine (SSP) and then given both Annexin 488 and Propidium Iodide (PI). Different phases of SSP-induced RGC death, are shown in stills of the same area of the eye followed up over several hours. Apoptosing single cells in the early (positive annexin 488 staining only) and late (positive annexin 488 & PI staining) apoptotic and necrotic (PI staining only) phases at 2.0 (a), 2.5 (b), and 3.0 (c) hours after SSP treatment can be seen. (d) Using this technique, it is possible to track changes in the same cells (arrowed and identified as Points 1 and 2) over time, undergoing the sequential stages of apoptotic cell death. Both cells show the peak in annexin 5 labelling occurs before that of PI, and substantiates the claim that wavelength optimisation of markers can lead to visualization of cell death in the eye.

FIG. 20 shows a comparison between in vivo MC540 labelling of eyes treated with saline and SSP and compared to Annexin Dy-776 labelling. As can be seen, Annexin Dy-776 is able to label single cells which are clearly individually visible in the in vivo images. The level of RGC apoptosis is much higher after SSP administration in the Annexin-Dy-776. In comparison, because the MC 540 labels whole membranes, a diffuse fluorescent signal is detected, making it impossible to identify single cells, although the MC540 after SSP image has a definitely higher level of fluorescence than baseline.

EXAMPLES

Conjugation of D776 to Annexin 5

Figure 1A:
FIG. 1a shows a comparison of in vivo imaging with histological retinal apoptosis in animal model of glaucoma at 3 weeks. The overlay of corresponding confocal microscopy (histology) over the in vivo image shows more apoptotic cells labelled with intravitreal Annexin-488 (grey spots in overlay) in histology image than in vivo image (white spots on background image).

Recombinant bacterially expressed annexin 5 (5 mg in 1 ml isotonic buffer) is dialysed against 'labelling buffer' over three hours with two changes (250 ml each time). The labeling buffer is produced by dissolving 21 g (250 mmol) of sodium hydrogen carbonate in 400 ml distilled water. 1 g of sodium azide (0.2 per cent) is added. The pH is adjusted with a concentrated aqueous solution of sodium hydroxide to pH 9.0. Prior to use, the buffer is diluted by addition of 9 parts water to one part of the concentrated stock solution (v/v). The annexin 5 protein is now ready for the labelling reaction. The dye to protein ratio is kept constant for each labelling reaction. Thus, 0.5 mg of the D-776-NHS-ester is used for labelling 1 mg of annexin 5. This provides a molar ratio between dye and annexin 5 protein of approximately 500. The NHS-ester is dissolved in dimethylformamide by vortexing, and the reaction started by adding the dye to annexin 5 protein in the labeling buffer. The final concentration of annexin 5 in the labeling reaction should be 5 mg/ml. Labelling is allowed to proceed in an Eppendorf tube placed in a shaker over the course of two hours.

At the end of the reaction period the coloured labelling solution is carefully pipetted onto a 5- or 10 ml column of Sephadex G-25 and allowed to seep into the gel. The conjugate is then eluted by slowly adding 100 mM PBS-buffer pH 7.4 drop by drop onto the column. The labelled protein runs ahead as a relatively sharp band while the free dye is slowly smearing behind. Once the conjugated annexin 5 arrives at the bottom of the column it is collected in an Eppendorf tube and is immediately ready for use.

Imaging Methods

Imaging may be carried out using techniques known in the art, such as those described in as follows:

All in vivo imaging was carried out with the DARC (Detection of Apoptosing Retinal Cells) technique[1] with a modified cSLO (confocal scanning laser opthalmoscope) at 790 nm (Heidelberg Retina Angiograph 2, Heidelberg Engineering, Dossenheim, Germany)[1, 2, 3]. The standard lens (15°×15° to 30°×30°) and the wide-field lens (55°-all degree values calibrated for the human eye) were used. Reflectance and corresponding fluorescent images with different focus settings were taken of the rat retina. To improve the signal-to-noise ratio and to enhance image contrast, the mean image out of a series of single images (up to 100) was calculated after correction of eye movements.

Optimising fluorescence

The inventors found that the presence of intrinsic fluorescent signals in the retina meant that cell death markers labelled with certain fluorescent labels could not be properly imaged. The inventors had previously used a fluorescent labelled annexin (Annexin 488) to image the apoptosis of retinal ganglion cells. When administered systemically the inventors found that surprisingly, inherent retinal autofluorescence interfered with the signal to such a degree that no useful results could be obtained.

Figure 1B:
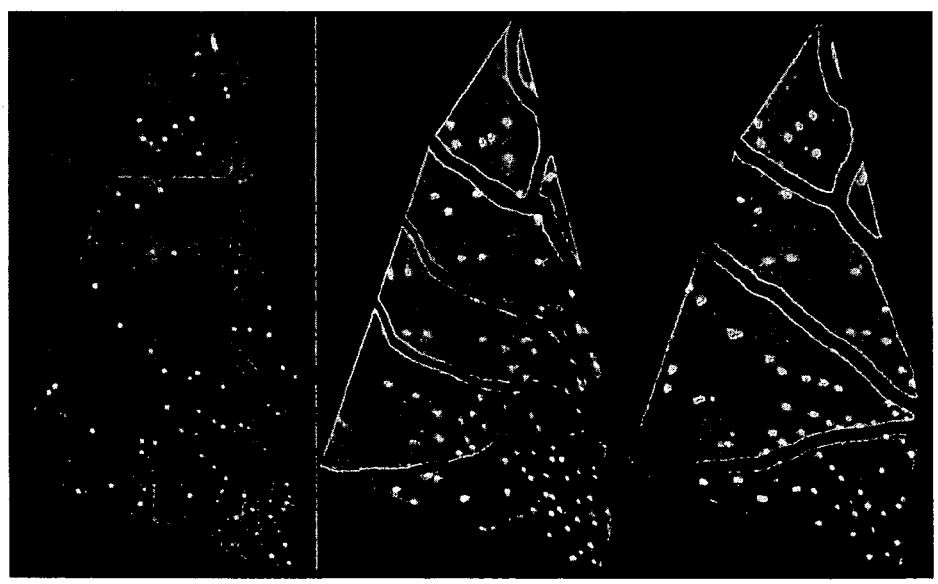
FIG. 1b shows images of corresponding areas of retina using histology, in vivo and ex vivo analysis in staurosporine treated rat eye using intravitreal Annexin Dy-776 (red-labelled spots). A 1:1 correlation between all three methods is clearly seen.
Figure 2A:
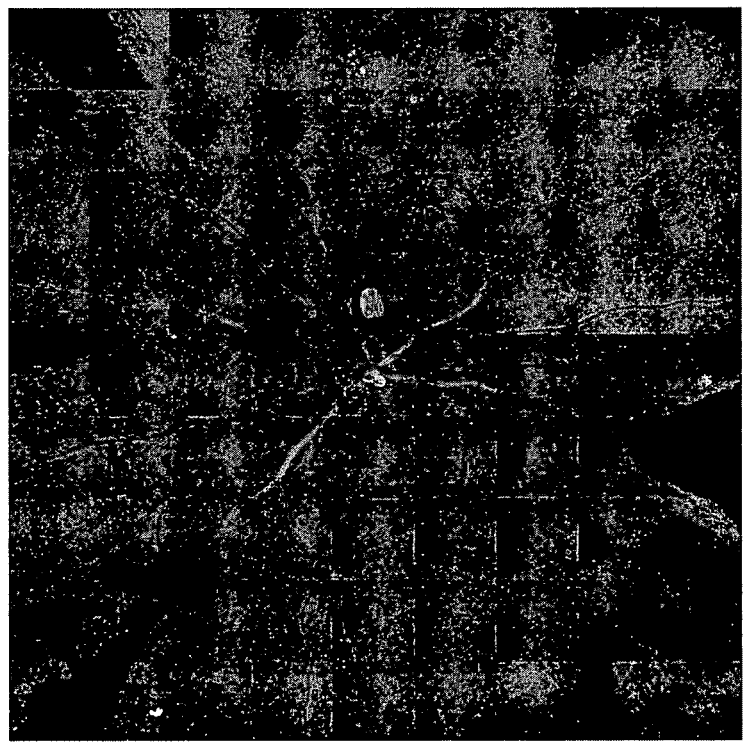
FIGS. 2a and 2b show DARC (Detection of Apoptosing Retinal Cells) retinal images demonstrating that intravenous Annexin 488 (125 ug) could not be visualized in vivo, even though histology images of SSP (a) and glaucoma (b) animals revealed apoptosis-proving the marker had crossed the blood retinal barrier. The inventors felt that in vivo imaging was not possible because of the high level of background autofluorescence encountered at this unoptimised wavelength.
Figure 2B:
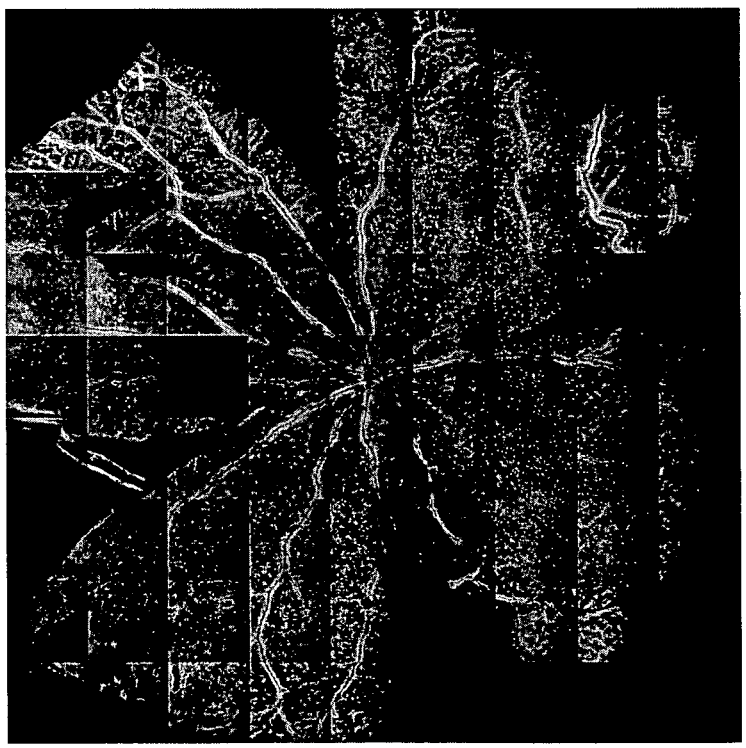
Figure 2C:
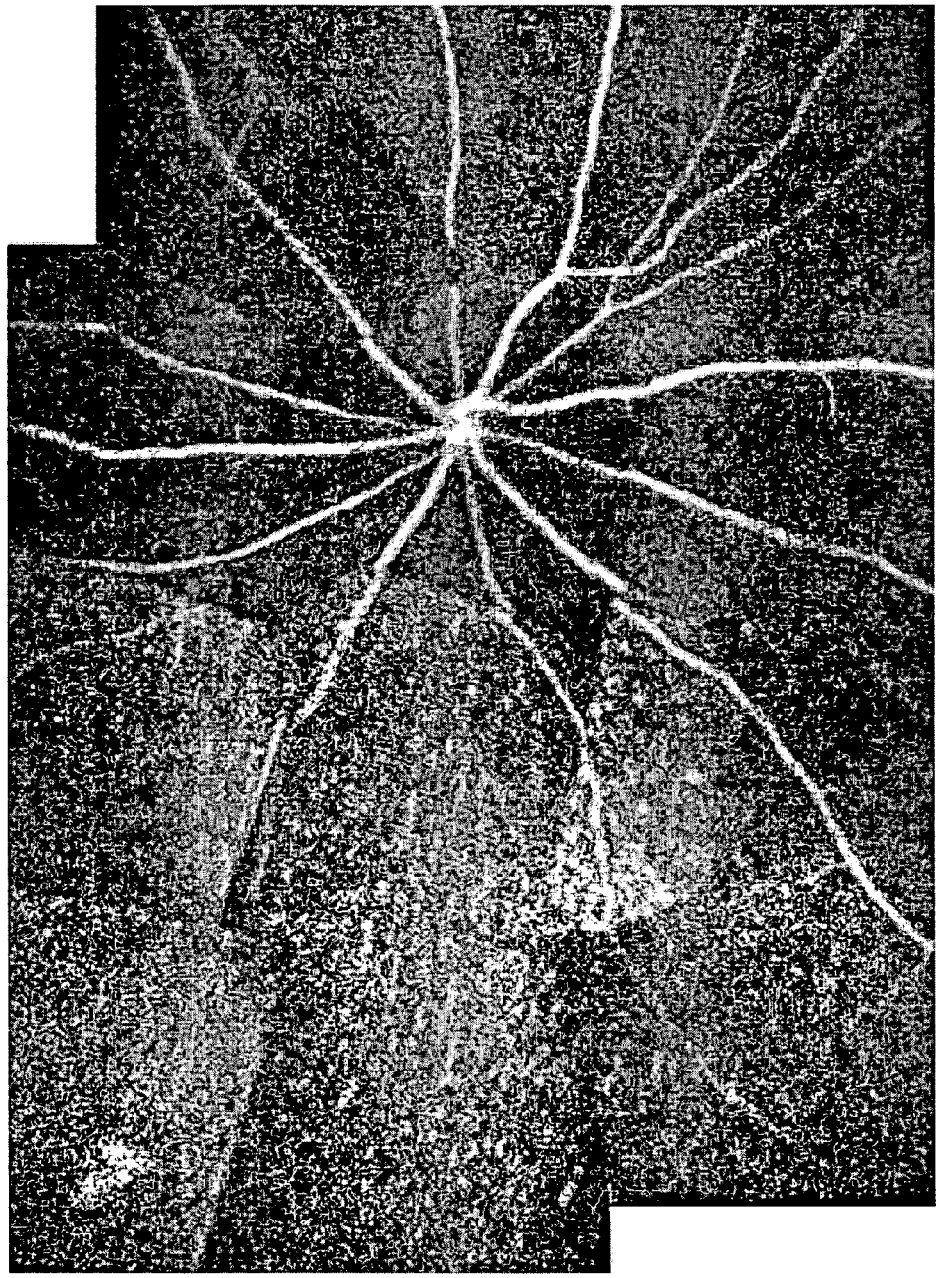
FIG. 2c shows that at optimised wavelengths, e g infrared, intravenous annexin-Dy-776 (125 ug) was able to show SSP-induced, single retinal cell apoptosis in vivo, and histologically.
Figure 3A:
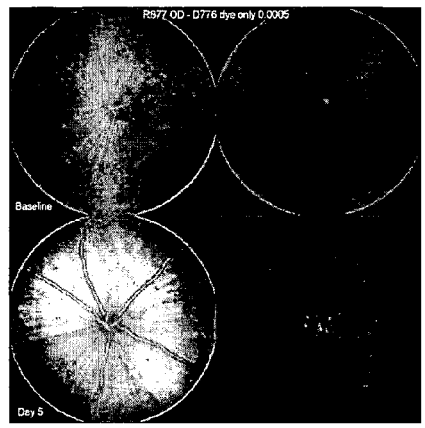
FIG. 3 shows reflective and DARC images of retinas treated with Dy-776 alone (A), 25 Annexin-Dy-776 (B) and Annexin IRDye800 (C) demonstrating that retinal vascular tortuosity in vivo may be seen using IRDye800 but not with Dy-776 (either singly or on repeated injection).
Figure 3B:
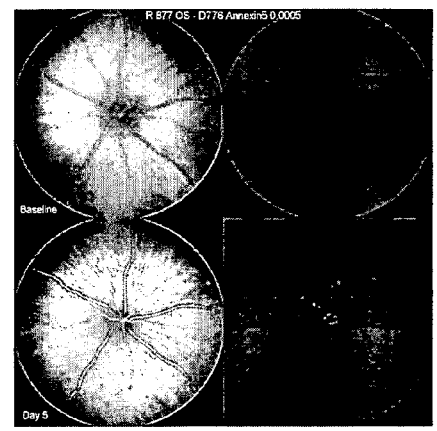
Figure 3C:
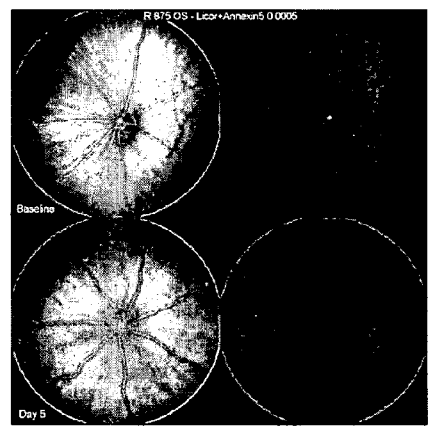

To avoid interference from retinal autofluorescence, inventors investigated other fluorophores including near-infrared and infrared fluorophores such as Licor 800 CW, Dy-776 and Dy-781. Using these labels, the inventors were able to see single cell apoptosis in the living eye that corresponded exactly to the histological localisation. This is illustrated in FIGS. 1, 2 and 3.

Figure 4:
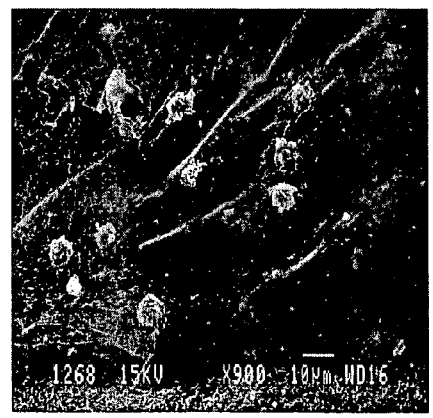
FIG. 4 is a scanning electron micrograph of an eye treated with IRDye 800 labelled annexin showing the presence of inflammatory cells in the vitreous base. A number of hyalocytes but also some inflammatory cells are seen in the vitreous.

In assessing the three dyes, the inventors found that both Licor 800 CW and Dy-781 caused vascular tortuosity and vitreous inflammation. Dy-776 did not cause inflammation or vascular changes. This is shown in FIGS. 3 and 4.

Assessment of Diabetic Neurodegeneration in Transgenic Models.

Figure 5A:
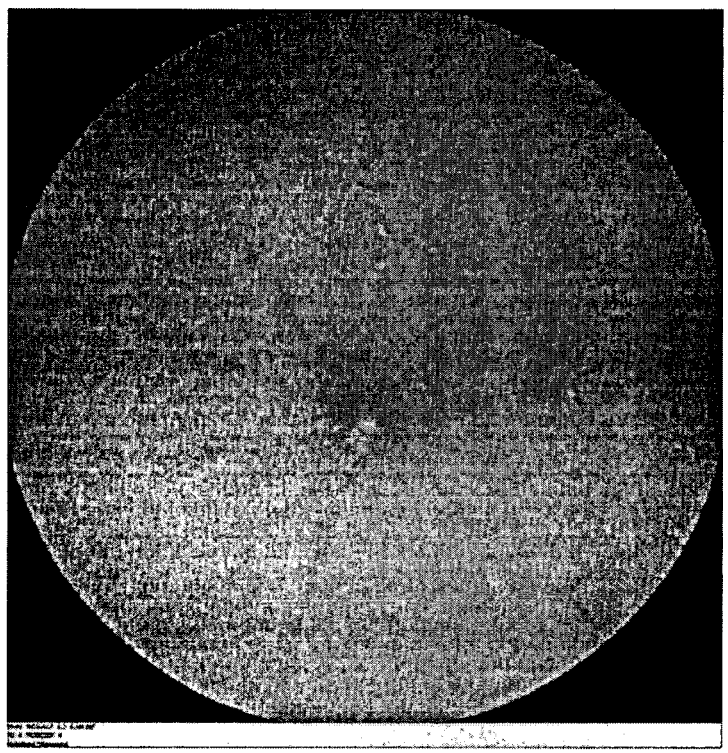
FIG. 5 shows the results of a DARC (Detection of Apoptosing Retinal Cells) assessment of diabetic neurodegeneration in transgenic models. Apoptotic retinal ganglion cells can be seen in the diabetic retina (a), but not in the wild type age-matched control (b).
Figure 5B:
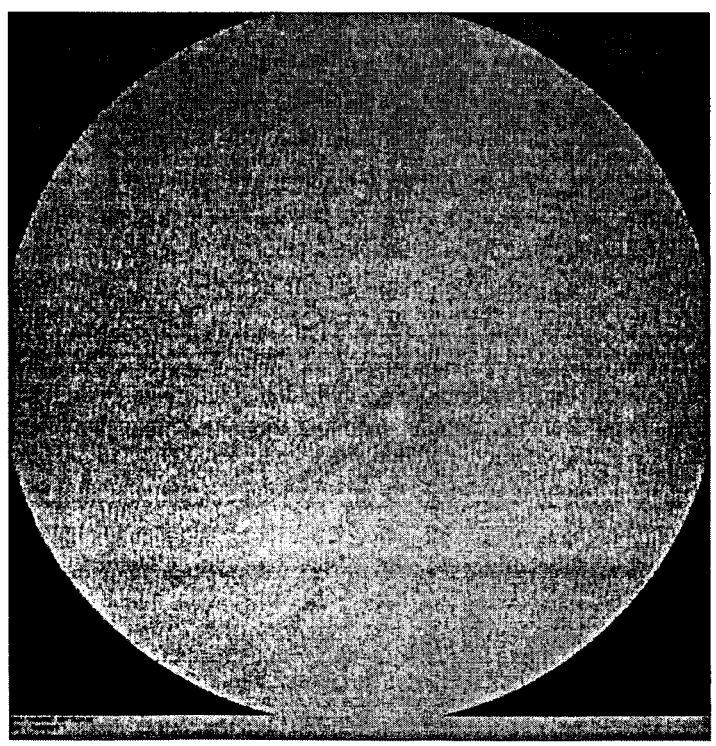
Figure 6:
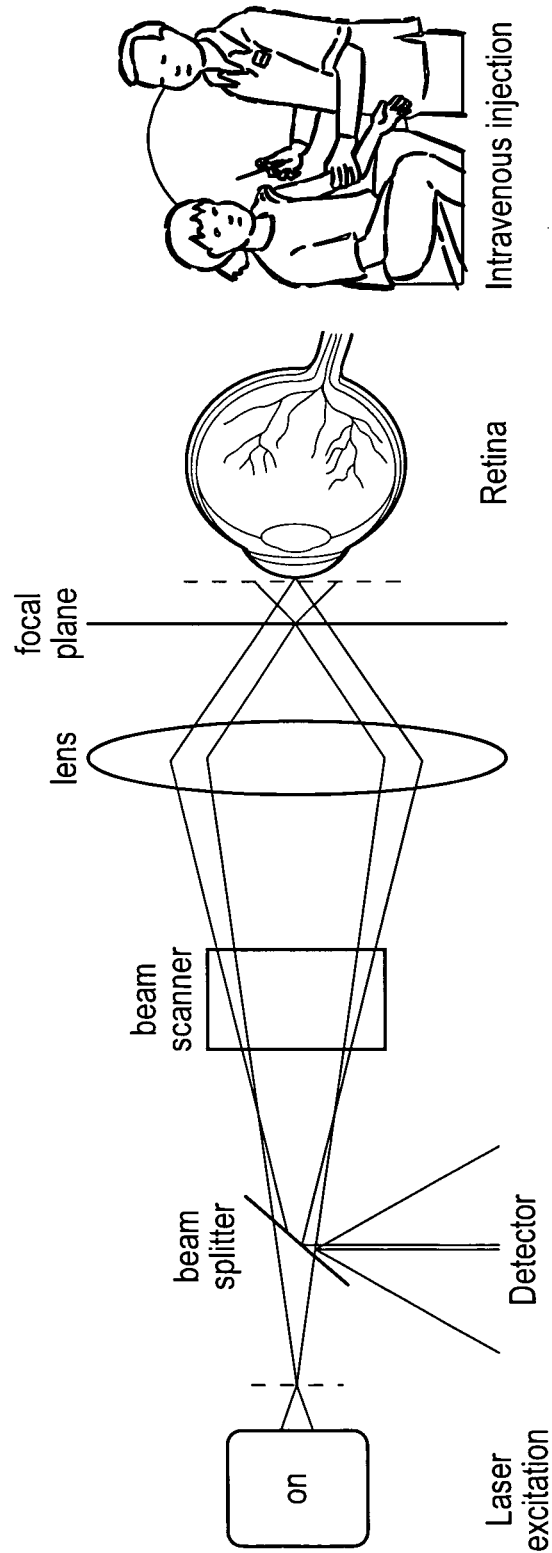
FIG. 6 shows the methodology for the technique of visualization of cell-death markers that are wavelength-optimised in the eye. Briefly, an intravenous injection (or ocular or topical or other mode) of the wavelength optimised dye is given, following which, after an optimal time, visualization of the retina is achieved following excitation with a laser light of optimised-wavelength and detection, with correct filters at optimised wavelengths.
Figure 7:
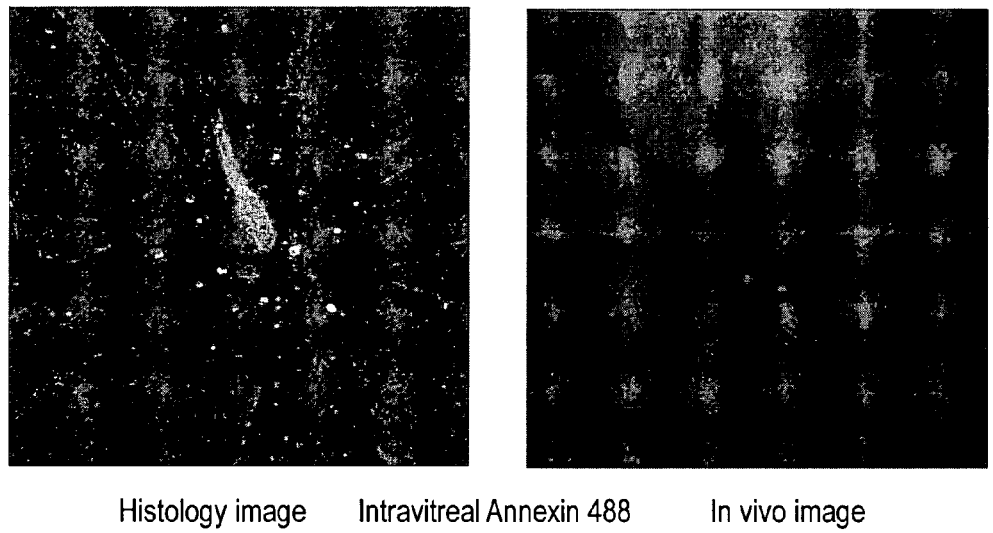
FIG. 7 shows images of corresponding areas of the same rat eye histologically and in vivo following intravitreal injections with staurosporine (7.14 nanomoles or 0.2 mg/ml) and Annexin 488. There is a surprising discrepancy between the number of positive spots (Annexin 488) imaged in vivo compared to the histology, with many more being seen histologically.
Figure 8:
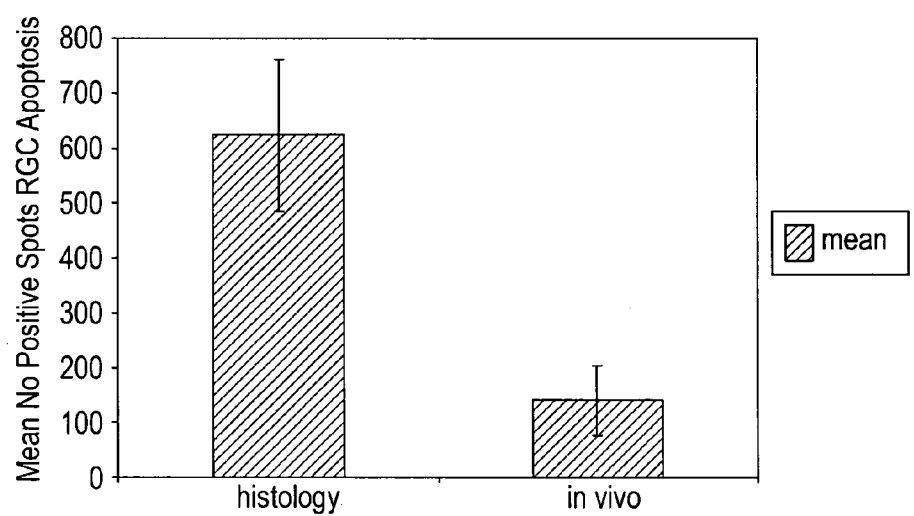
FIG. 8 is a graph showing the mean counted intravitreally administered Annexin 488 positive spots histologically compared to positive spots of RGC apoptosis seen in vivo of corresponding images taken for 3 eyes following SSP treatment. There is a significant higher count in the histological image.
Figure 9:
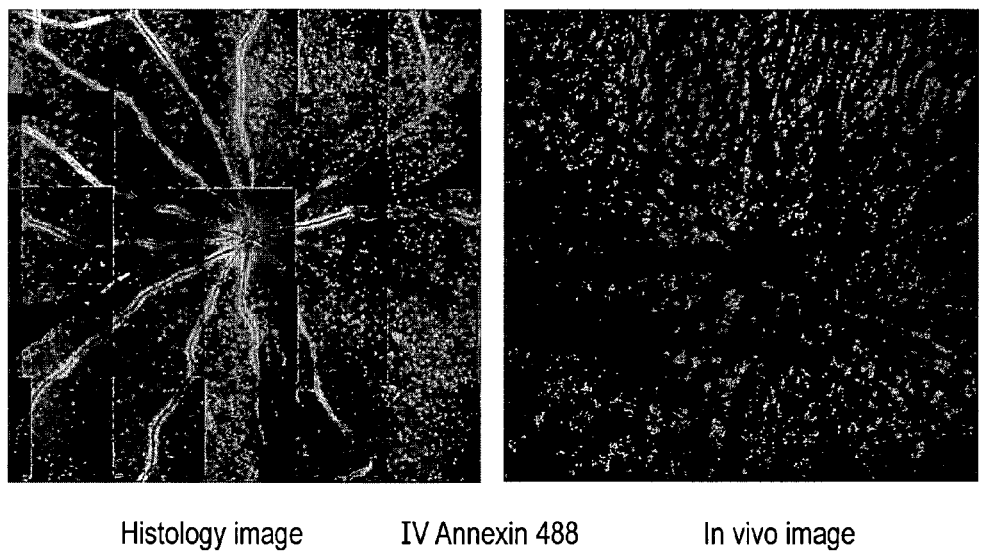
FIG. 9 shows the results of the intravenous administration of Annexin 488 (0.2 ml 25 ug/ml) in an SSP-treated eye. The eye showed Annexin 488 positive spots histologically but nothing in vivo.
Figure 10:
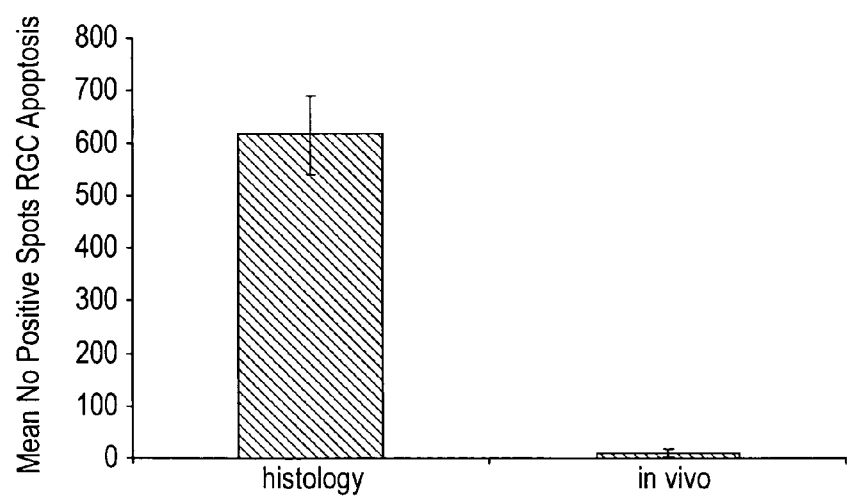
FIG. 10 shows the results of administration of intravenous Annexin 488. In particular, there were similar mean counts of Annexin 488 positive spots histologically when compared to intravitreal Annexin 488, but very little was visualized in vivo.

A DARC assessment of diabetic neurodegeneration in transgenic models was carried out using techniques described herein. As seen in FIG. 5, the diabetic animal (a) shows significantly more retinal ganglion cell apoptosis than the age-matched wild type control (b).

Wavelength Optimisation of Fluorescently Tagged Annexin 5 (Anx-F)

In vivo v. Histology Discrepancy in Labelled Cells a) Intravitreal Administration The inventors had previously used a fluorescent labelled annexin 5 (Annexin 488) to image the apoptosis of retinal ganglion cells which was administered into the eye intravitreally. Alexa Fluora 488-labelled annexin 5, or annexin 5 tagged to another fluorescent marker. They assessed:

Annexin Alexa Flour 532 excitation/emission maxima of 532/553

Annexin Alexa Fluor 555 excitation/emission maxima of 555/568

Annexin Dy-776 excitation/emission maxima of 771/793

Annexin Dy-781 excitation/emission maxima of 783/800

Annexin Licor IRDye800 excitation/emission maxima of 774/789

The inventors also found that the number of dye molecules conjugated per Annexin molecule was important. The inventors argue that aiming for a low number of dye molecules (fewer than 12 and preferably fewer than 5) per Annexin molecule enhances the native fluorescence of the conjugate whilst retaining its binding affinity for apoptotic cells.

The inventors also found that how the dye molecule was conjugated to the Annexin molecule was important. The inventors found that labelling the Annexin molecule with the dye at the N-terminus resulted in improved signal-to-noise, and when administered intravenously resulted in less major organ uptake, for example to the liver and kidney. Furthermore, labelling cysteine residues rather than lysine residues in the Annexin molecule resulted in less noise.

Figure 11:
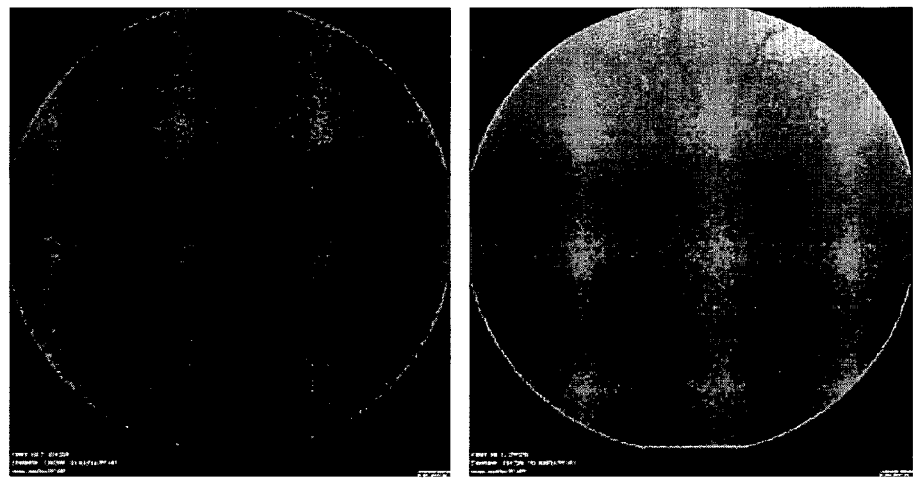
FIG. 11 shows in vivo DARC images using Annexin Alexa Fluor 555 of the same eye at baseline and 2 hours after staurosporine (SSP) administration. White spots showing apoptosis are seen in vivo-but very faintly.
Figure 12:
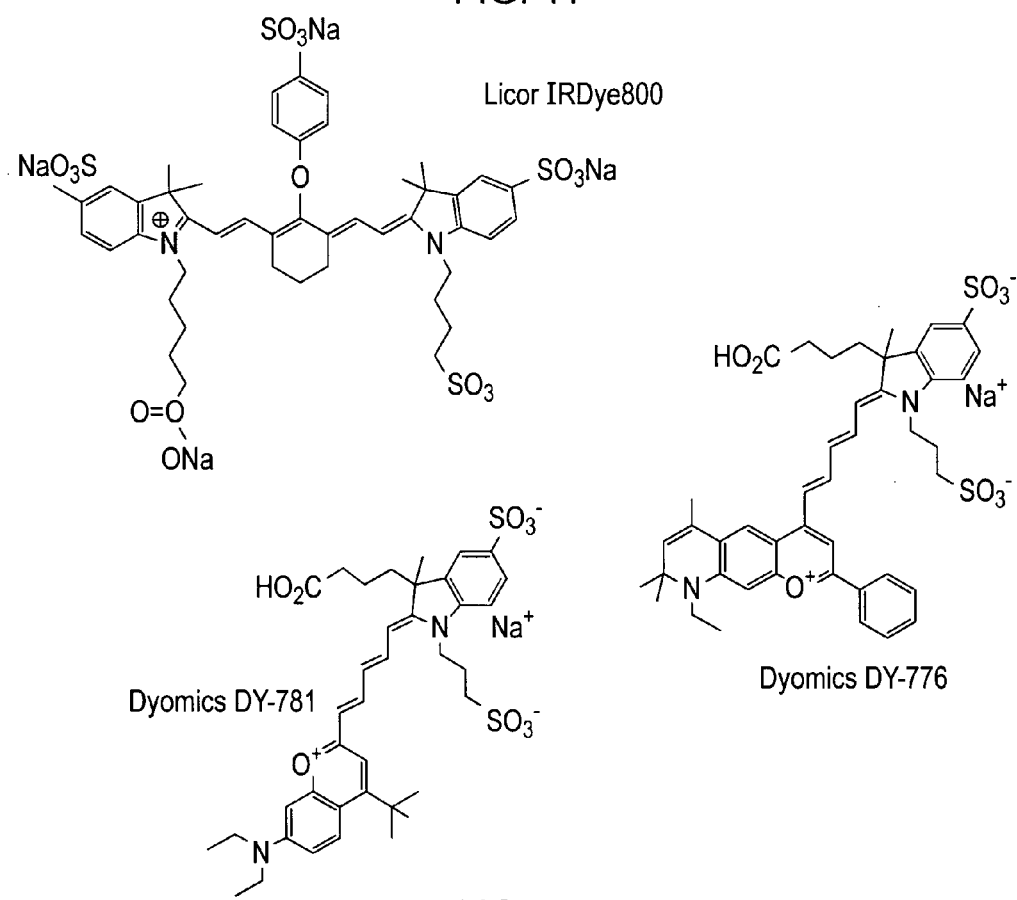
FIG. 12 shows the molecular structure of three of the infrared dyes used.

The images in FIG. 11 show in vivo DARC using Annexin Alexa Fluor 555 of the same eye at baseline and 2 hours after staurosporine (SSP) administration. White spots showing apoptosis are seen in vivo-but very faintly. Compared to the infrared dyes (see below), both Annexin Alexa Fluor 555 and Annexin Alexa Fluor 532 were clearly suboptimal for in vivo imaging with DARC.

Surprisingly, of all the fluorescent tags assessed, the best coupled dye with Annexin 5 was Dy-776. It showed perfect correlation (1:1) with in vivo imaging and histology with Annexin Dy-776, as seen below.

Statistical analysis comparing histology to in vivo, using separation distance between points, the mean separation was 19.756 pixels in the images above, compared to a random noise model (30.986 pixels), and the probability of this occurring by chance is 0.001305 percent. A similar result was obtained with matching individual points-with p=0.001597 percent-i.e. it is highly unlikely that the matching of points between histology & in vivo images could have occurred by chance. This is to be compared with the other infra-red annexin dyes, such as the IRDye800 (Licor) which showed at least 20% fewer spots in vivo.

Use of Annexin Dy-781 gave similar results, but as with the Annexin IRDye 800, imaging 5 days after the dye was given revealed retinal vascular tortuosity-suggesting inflammation.

Figure 13:
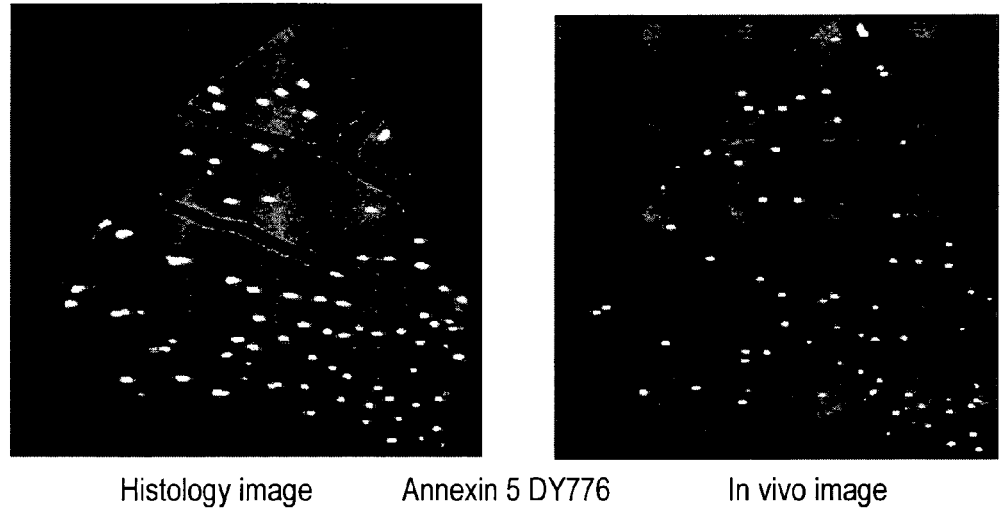
FIG. 13 shows the results of an assessment of fluorescent tags. Of all the fluorescent tags assessed, the best coupled dye with Annexin 5 was Dy-776. It showed perfect correlation (1:1) with in vivo imaging and histology with Annexin Dy-776.
Figure 14:
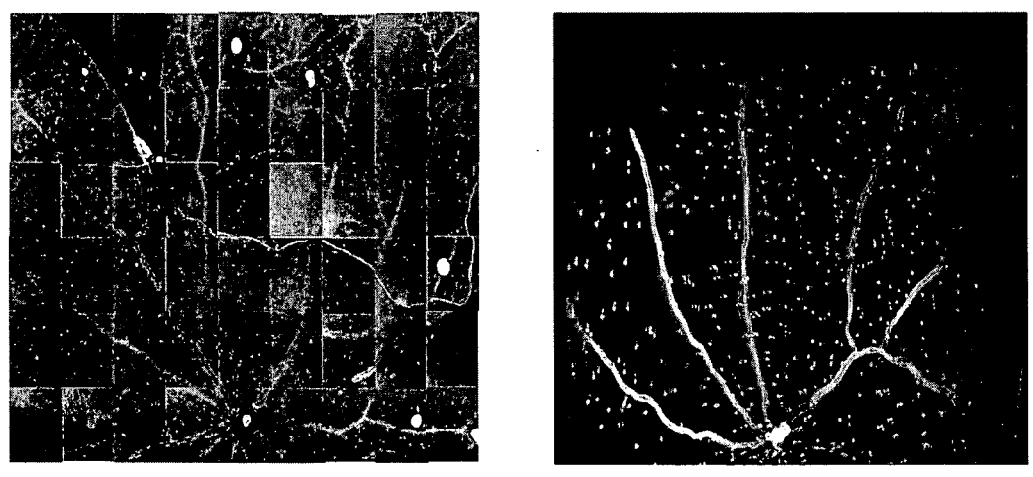
FIG. 14 shows the results of the administration of Annexin labelled with IRDye800. Administration of Annexin IRDye800 to a model of glaucoma showed increased in vivo retinal cell apoptosis labelling. There was still however a 20% reduction in the level of labelling in vivo compared to histologically.
Figure 15:
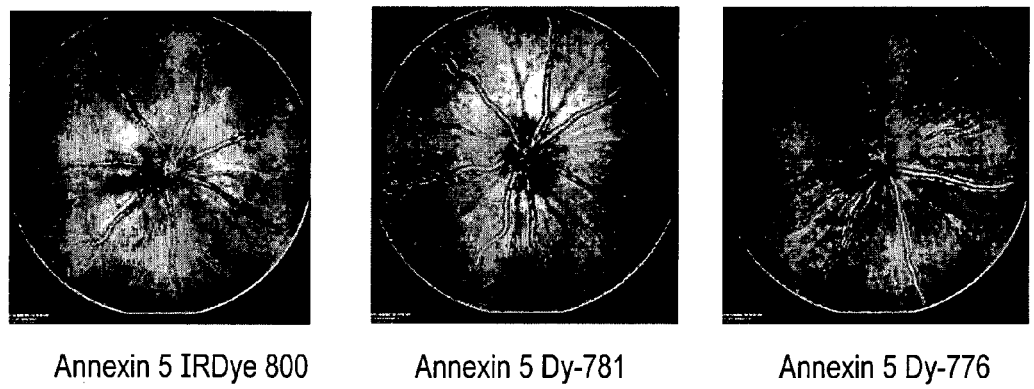
FIG. 15 is reflective images showing rat eyes treated with the same dose of Annexin 5 conjugated with different infrared fluorescent dyes 5 days after administration. Only the eye treated with Annexin 5 Dy-776 showed no retinal vessel tortuosity at this time point.

The images in FIGS. 13, 14 and 15 show rat eyes treated with the same dose of Annexin 5 conjugated with different infra-red fluorescent dyes 5 days after administration. Only the eye treated with Annexin 5 Dy-776 showed no retinal vessel abnormalities.

Figure 16:
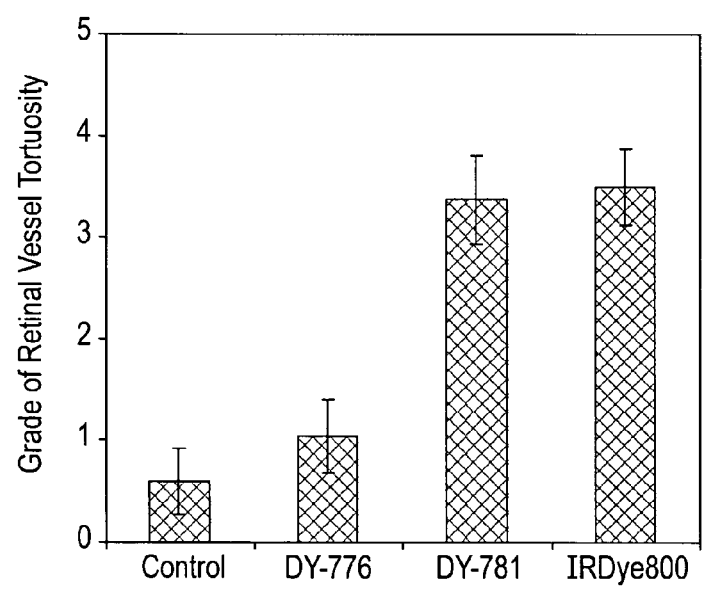
FIG. 16 is a graph showing the difference observed in the level of retinal tortuosity as graded by blinded observers looking at in vivo pictures. There was a significant increase in vessel tortuosity in eyes given intravitreal IRDye800 and Dy-781 compared to Dy-776 and control. This occurrence strongly suggested inflammation.

The graph in FIG. 16 shows the difference observed in the level of retinal tortuosity as graded by blinded observers looking at in vivo pictures. There was a significant increase in vessel tortuosity in eyes given intravitreal IRDye800 and Dy-781 compared to Dy-776 and control. This occurrence strongly suggested inflammation, which was investigated next in conjunction with histology.

Figure 17:
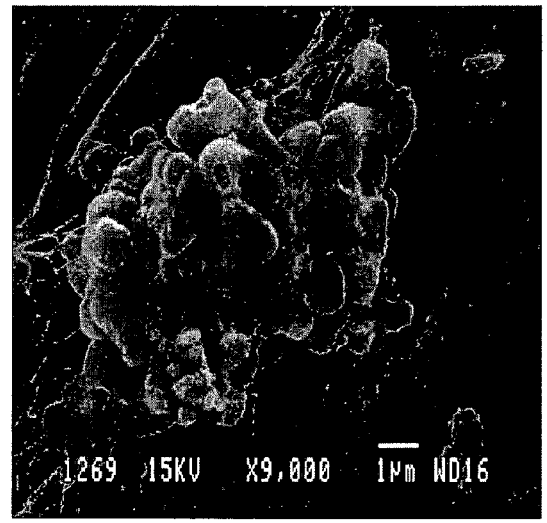
FIG. 17 is a scanning electron microscopy image of a macrophage found in the vitreous of an eye with Annexin 5 IRDye 800-which confirms the presence of inflammation caused by the dye.

FIG. 17 is a scanning electron microscopy image of a macrophage observed in the vitreous of an eye with Annexin 5 IRDye 800, which confirms the presence of inflammation caused by the dye.

Use of Other Annexins as Markers

We have shown that other Annexin Markers such as Annexin 11, Annexin 2 and Annexin 6, which all have affinity for exposed phosphatidylserine, also bind to apoptosing retinal cells.

Figure 18:
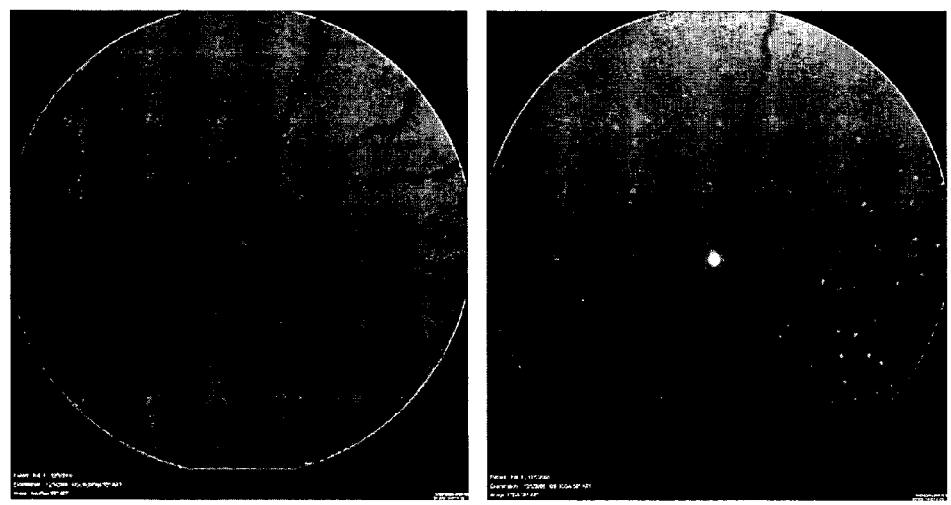
FIG. 18 shows in vivo DARC images using Annexin 11 Dy-776 of the same eye at baseline and 2 hours after staurosporine (SSP) administration. The white spots clearly demonstrate that Annexin 11 may be used to detect apoptosis in vivo.

The images in FIG. 18 show in vivo DARC images using Annexin 11 Dy-776 of the same eye at baseline and 2 hours after staurosporine (SSP) administration. The white spots clearly demonstrate that Annexin 11 may be used to detect apoptosis in vivo.

Use of Other (i.e. Not Annexin) Markers of Cell Death
Propidium Iodide

The inventors next assessed other markers of cell death. Firstly, Propidium Iodide (PI) which identifies necrotic cells by labelling cells with disrupted membranes and fluorescently staining their DNA and RNA. PI has excitation and emission maxima of 532 nm and 649 nm respectively. The images in FIG. 19 show a comparison between in vivo PI labelling necrotic cells and Annexin 488 labelling apoptosing cells in vivo in the retina.

(a-c) Stills taken from a time lapse video of staurosporine (SSP)-induced RGC death, showing single cells in the early (green, positive annexin 488 staining only) and late (yellow, positive annexin 488 & PI staining) apoptotic and necrotic (red, PI staining only) phases at 2.0 (a), 2.5 (b), and 3.0 (c) hours after SSP treatment. (d) Using this technique, it is possible to track changes in the same cells (arrowed and identified as Points 1 and 2) over time, undergoing the sequential stages of apoptotic cell death. Both cells show the peak in annexin 5 labelling occurs before that of PI, and substantiates the claim that wavelength optimisation of markers can lead to visualization of cell death in the eye.

The inventors also found that simultaneous visualisation of multiple cell death markers such as Annexin V and Propidium Iodide is possible as long as each separate marker has been wavelength optimised.

Merocyanine 540 (MC540)

Merocyanine 540 is a dye that identifies apoptotic cells by virtue of the fact that it binds to the outer membrane of cells and fluoresces in proportion to the degree of disorganisation of the membranes, which occurs early in apoptosis. MC450 has excitation and emission maxima of 488 nm and 575 nm respectively. The images in FIG. 20 show a comparison between in vivo MC540 labelling of eyes treated with saline and SSP and compared to Annexin 776 labelling.

As can be seen, Annexin 776 is able to label single cells which are clearly individually visible in the in vivo images shown above. The level of RGC apoptosis is much higher after SSP administration. In comparison, because the MC 540 labels whole membranes, a diffuse fluorescent signal is detected, making it impossible to identify single cells, although the MC540 after SSP image has a definitely higher level of fluorescence than baseline.

Labelling Apoptosing Cells Throughout the Retina

Figure 21:
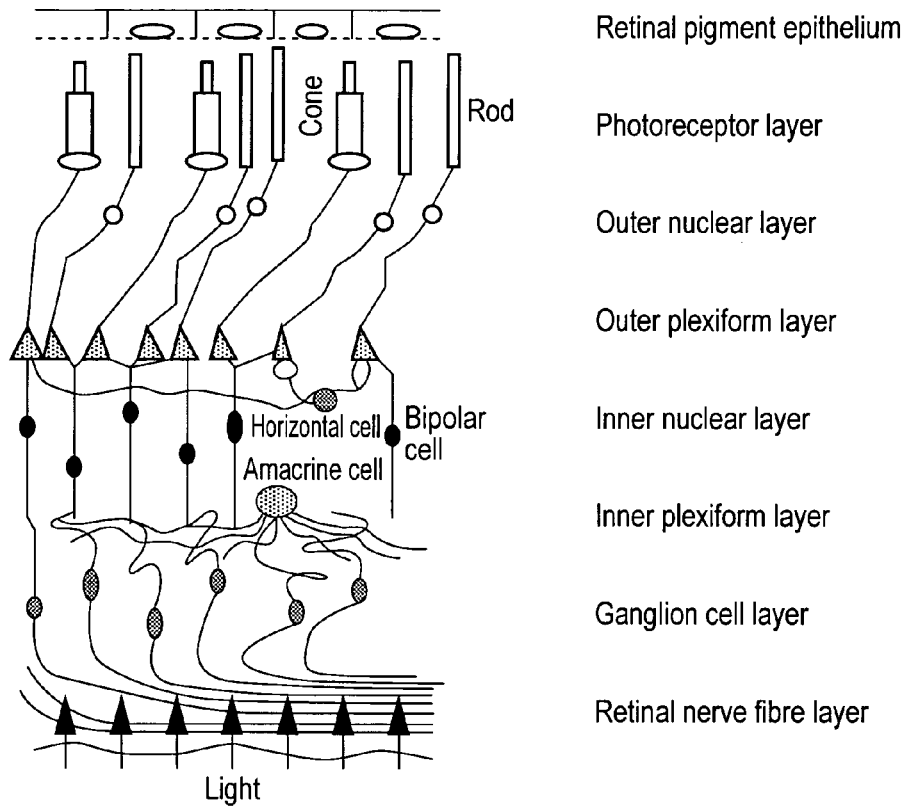
FIG. 21 is a diagram showing retinal layers. The retinal nerve cells are: photoreceptors, bipolar, horizontal, amacrine and ganglion cells.

The inventors have previously shown that Anx-F may be used to identify RGC apoptosis. More recently, using the same technique, they have shown it is possible to visualise apoptosing bipolar cells. They now show, that Anx-F when given intravitreally, can also stain other retinal cells, as seen in FIG. 21.

Figure 22:
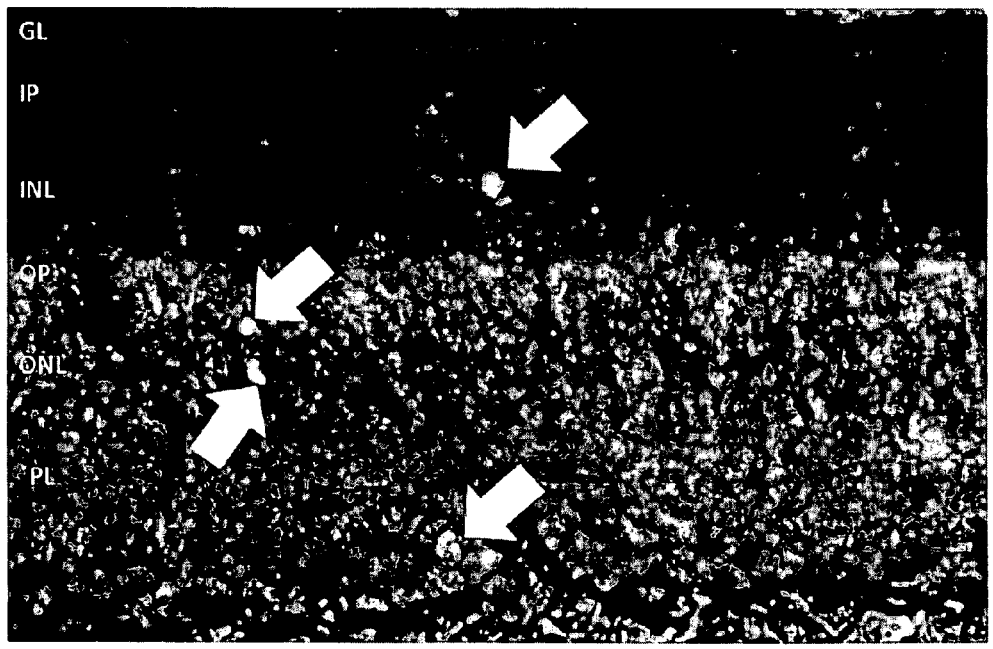
FIG. 22 shows a histology section of the retina of a mouse model of ischaemia. Intravitreal Anx-F was given before the animal was killed. The arrows show four cells stained positive for Anx-F in different layers of the retina-confirming the presence of apoptosis in the inner nuclear (INL), outer nuclear (ONL) and photoreceptor layers (PL).

The histology section in FIG. 22 is taken from a mouse eye which has had ischaemia induced experimentally. Intravitreal Anx-F was given before the animal was killed. The arrows show four cells stained positive for Anx-F in different layers of the retina—confirming the presence of apoptosis in the inner nuclear (INL), outer nuclear (ONL) and photoreceptor layers (PL).

REFERENCES

1. Cordeiro M F, Guo L, Luong V, et al. Real-time imaging of single nerve cell apoptosis in retinal neurodegeneration. *Proc Natl Acad Sci USA* 2004; 101: 13352-13356.
2. Guo L, Salt T E, Luong V, et al. Targeting amyloid-{beta} in glaucoma treatment. *Proc Natl Acad Sci USA* 2007.
3. Maass A, Lundt von Leithner P, Luong V, et al. Assessment of rant and mouse RGC apoptosis imaging in-vivo with different scanning laser opthalmoscopes. *Curr Eye Res* 2007; [accepted for publication].

The invention claimed is:

1. A method for identifying cell death in the eye, comprising providing a composition comprising a cell death marker labeled with a wavelength-optimized label, wherein the cell death marker is an annexin and the wavelength-optimized label is Dy-776 having the structure:

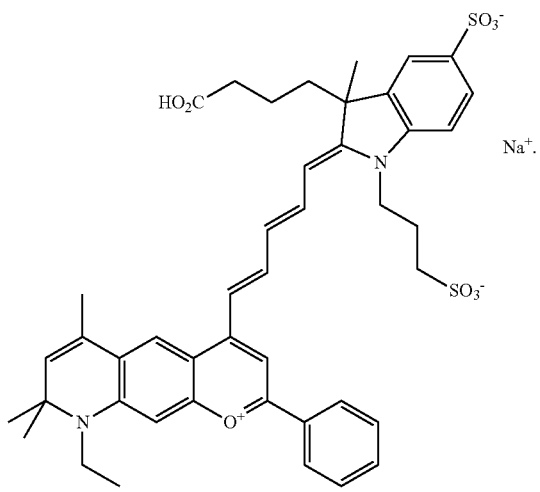

or Dy-781 having the structure:

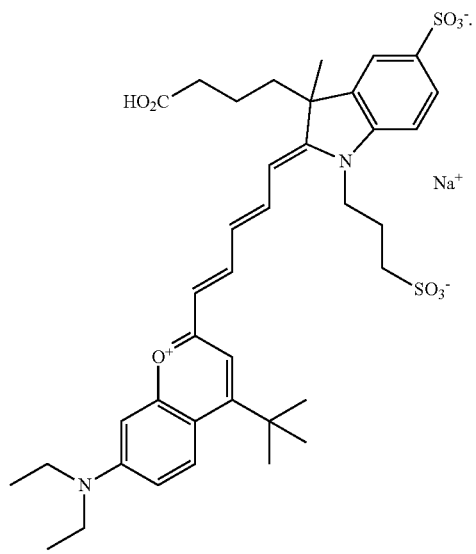

2. The method of claim 1, wherein the cell death marker is annexin 5, 11, 2 or 6.

3. The method of claim 1, wherein the wavelength-optimized label is Dy-776.

4. The method of claim 1, wherein the marker is for identifying retinal cell death.

5. The method of claim 4, wherein the marker is for identifying retinal nerve cell death.

6. The method of claim 1, wherein the marker is for identifying single cell death.

7. A method for monitoring cell death in the eye, comprising the steps of:
(a) administering a composition comprising a cell death marker labeled with a wavelength-optimized label to a subject, wherein the cell death marker is an annexin and the wavelength-optimized label is Dy-776 having the structure:

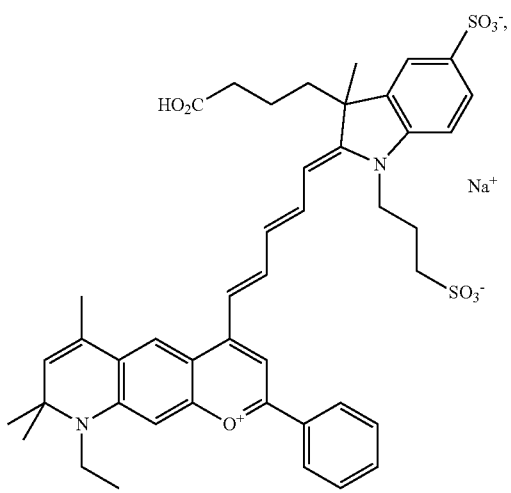

or Dy-781 having the structure:

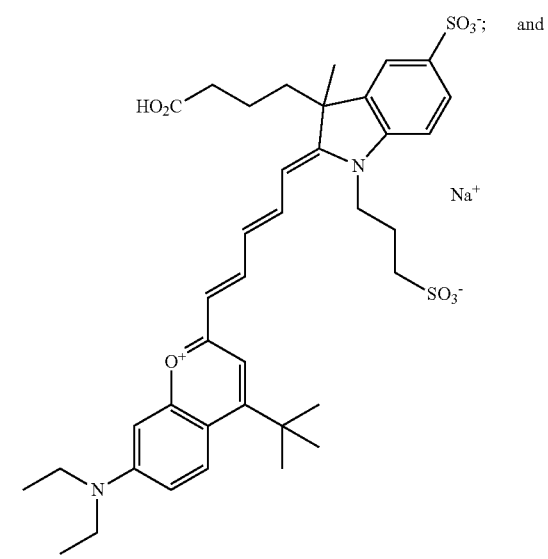

(b) generating an image of emission wavelength from the subject's eye using an imaging device; wherein the image is a representation of cell death in the eye.

8. The method of claim 7, wherein the cell death marker is an annexin.

9. The method of claim 8, wherein the cell death marker is annexin 5.

10. The method of claim 8, wherein the wavelength-optimised label is Dy-776.

11. The method of claim 7, wherein the marker is for identifying retinal cell death.

12. The method of claim 11, wherein the marker is for identifying retinal nerve cell death.

13. The method of claim 7, wherein the marker is for identifying single cell death.

14. The method of claim 7, wherein the labeled marker is administered systemically, topically or ocularly.

15. The method of claim 7, wherein the step of generating an image is repeated.

16. The method of claim 15, wherein the step of generating and image is repeated to allow real time imaging.

17. The method of claim 7, wherein the method is for diagnosing a degenerative disease of the eye.

18. The method of claim 17, wherein the disease is glaucoma or diabetic retinopathy.

19. The method of claim 7, wherein the disease is a neurodegenerative disease of the brain.

20. The method of claim 19, wherein the disease is Alzheimer's disease.

21. A composition comprising a cell death marker labeled with a wavelength-optimized label, wherein the cell death marker is an annexin and the wavelength-optimized label is Dy-776 having the structure:

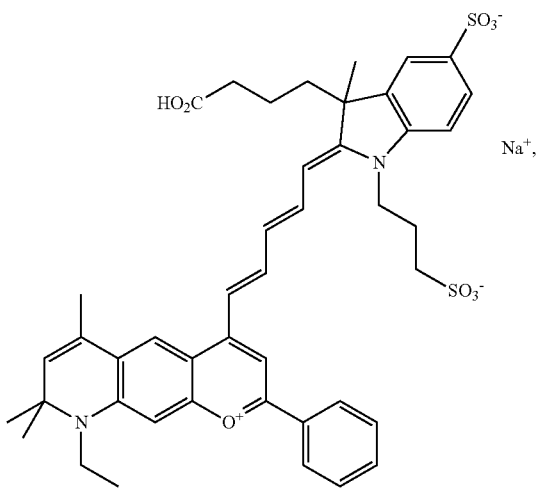

or Dy-781 having the structure:

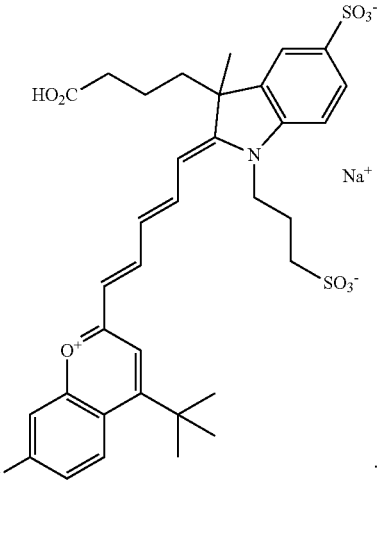

22. The composition of claim 21, wherein the composition is in a form suitable for intravenous, ocular or topical administration.

23. The composition of claim 21, wherein the cell death marker is annexin 5, 11, 2 or 6.

24. The composition of claim 21, wherein the wavelength-optimized label is Dy-776.

* * * * *

UNITED STATES PATENT AND TRADEMARK OFFICE
CERTIFICATE OF CORRECTION

PATENT NO. : 8,771,645 B2
APPLICATION NO. : 12/808012
DATED : July 8, 2014
INVENTOR(S) : Cordeiro et al.

It is certified that error appears in the above-identified patent and that said Letters Patent is hereby corrected as shown below:

On the title page, item (73) Assignee: change from "UCL Business PLLC" to "UCL Business plc".

Signed and Sealed this
Seventeenth Day of November, 2015

Michelle K. Lee
*Director of the United States Patent and Trademark Office*